(12) United States Patent
Takatori et al.

(10) Patent No.: US 11,484,675 B2
(45) Date of Patent: Nov. 1, 2022

(54) AIRWAY ADAPTOR, BIOLOGICAL INFORMATION ACQUIRING SYSTEM, AND OXYGEN MASK

(71) Applicant: NIHON KOHDEN CORPORATION, Tokyo (JP)

(72) Inventors: Fumihiko Takatori, Tokyo (JP); Shinji Yamamori, Tokyo (JP); Masayuki Inoue, Tokyo (JP); Kota Saeki, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 864 days.

(21) Appl. No.: 13/968,499

(22) Filed: Aug. 16, 2013

(65) Prior Publication Data
US 2014/0066800 A1     Mar. 6, 2014

(30) Foreign Application Priority Data

Sep. 4, 2012  (JP) .............................. JP2012-194507
Dec. 12, 2012  (JP) .............................. JP2012-271719

(51) Int. Cl.
*A61M 16/06* (2006.01)
*A61B 5/083* (2006.01)
(Continued)

(52) U.S. Cl.
CPC ......... *A61M 16/0666* (2013.01); *A61B 5/082* (2013.01); *A61B 5/0826* (2013.01); *A61B 5/0836* (2013.01); *A61B 5/097* (2013.01); *A61B 5/4818* (2013.01); *A61B 5/682* (2013.01); *A61B 5/6803* (2013.01); *A61B 5/6819* (2013.01); *A61B 2562/0247* (2013.01); *A61B 2562/0271* (2013.01)

(58) Field of Classification Search
CPC ..................................................... A61B 5/0836
See application file for complete search history.

(56) References Cited

U.S. PATENT DOCUMENTS 6,165,133 A * 12/2000 Rapoport ............. A61B 5/0878
                                                                600/529
8,915,861 B2   12/2014 Yamamori et al.
(Continued)

FOREIGN PATENT DOCUMENTS

JP     H-0239755 U    3/1990
JP     2002-345781 A  12/2002
(Continued)

OTHER PUBLICATIONS

Extended European Search Report for the related European Patent Application No. 13181808.0 dated Oct. 17, 2013.
(Continued)

*Primary Examiner* — Jay B Shah
(74) *Attorney, Agent, or Firm* — Pearne & Gordon LLP

(57) ABSTRACT

An airway adaptor includes: a gas passage into which a respiratory gas of a subject is to flow; a respiratory gas introducing portion which is configured to guide the respiratory gas expired from at least one of nostrils and a mouth of the subject, to the gas passage; and an airway case on which a temperature sensor that is configured to detect a temperature change of the respiratory gas flowing into the gas passage is mountable.

26 Claims, 12 Drawing Sheets

(51) Int. Cl.
  *A61B 5/00* (2006.01)
  *A61B 5/08* (2006.01)
  *A61B 5/097* (2006.01)

(56) References Cited

U.S. PATENT DOCUMENTS

| | | | |
|---|---|---|---|
| 2004/0028118 A1* | 2/2004 | Sidoni | G01K 1/143 |
| | | | 374/E1.019 |
| 2004/0206907 A1* | 10/2004 | Yamamori | A61B 5/0836 |
| | | | 250/343 |
| 2005/0001728 A1* | 1/2005 | Appelt | G08B 21/182 |
| | | | 340/573.1 |
| 2006/0249160 A1 | 11/2006 | Scarberry et al. | |
| 2008/0190436 A1 | 8/2008 | Jaffe et al. | |
| 2009/0069646 A1 | 3/2009 | Yamamori et al. | |
| 2009/0088657 A1 | 4/2009 | Shinji et al. | |
| 2009/0133699 A1* | 5/2009 | Nalagatla | A61B 5/0836 |
| | | | 128/205.27 |
| 2009/0299158 A1* | 12/2009 | Boatner | A61B 5/01 |
| | | | 600/301 |
| 2009/0306528 A1 | 12/2009 | Curti et al. | |
| 2009/0306529 A1* | 12/2009 | Curti | A61B 5/0878 |
| | | | 600/537 |
| 2010/0145166 A1* | 6/2010 | Pickier | A61B 5/16 |
| | | | 600/301 |
| 2010/0168600 A1 | 7/2010 | Adriance et al. | |
| 2010/0168601 A1 | 7/2010 | Adriance et al. | |
| 2011/0301484 A1 | 12/2011 | Curti et al. | |
| 2012/0209096 A1 | 8/2012 | Jaffe et al. | |
| 2014/0094669 A1 | 4/2014 | Jaffe et al. | |

FOREIGN PATENT DOCUMENTS

| | | |
|---|---|---|
| JP | 2003-315264 A | 11/2003 |
| JP | 3133653 U | 7/2007 |
| JP | 2009-172347 A | 8/2009 |
| JP | 2009-545408 A | 12/2009 |
| JP | 2011-522618 A | 8/2011 |

OTHER PUBLICATIONS

Japanese Office Action for Application No. 2012-271719 dated Mar. 8, 2016.
"Sensor for Analyzing Sleep, Air Flow Sensor (Adult Size) TR-101A"; Catalog made on Feb. 23, 2011; Nihon Kohden Corporation; Internet <URL://www.nihonkohden.co.jp/iryo/documents/pdf/H902599.pdf> (Please see Specification pp. 2-3 for statement of relevance).
Japanese Office Action issued in Patent Application No. 2012-271719 dated Sep. 6, 2016.
European Communication pursuant to Article 94(3) EPC issued in Patent Application No. 13 181 808.0 dated Jul. 30, 2019.

* cited by examiner

AIRWAY ADAPTOR, BIOLOGICAL INFORMATION ACQUIRING SYSTEM, AND OXYGEN MASK

CROSS-REFERENCE TO RELATED APPLICATION(S)

This application is based upon and claims the benefit of priority from prior Japanese patent applications No. 2012-194507 filed on Sep. 4, 2012 and No. 2012-271719 filed on Dec. 12, 2012, the entire contents of which are incorporated herein by reference.

BACKGROUND

The presently disclosed subject matter relates to an airway adaptor which is mounted on the face of the subject to collect information of respiration, to a biological information acquiring system for acquiring various kinds of biological information by using the airway adaptor, and to an oxygen mask.

As a method of checking an occurrence of an apnea condition during sleep, there are methods in which biological information of the subject is acquired by using brain waves, an electromyogram, the blood oxygen saturation, respiration, or the like as a parameter, thereby checking such an occurrence. In the methods, as an example of collecting biological information related to respiration, there is a method in which biological information related to respiration is acquired based on a temperature change of the respiratory gas of the subject by using a temperature sensor.

An example of a temperature sensor is one which is to be mounted on the face (below the nose) of the subject, and the state of the respiratory gas during sleep is detected from a temperature change of the respiratory gas (see Non-patent Reference 1). In the sensor, two nose heat sensitive portions, one mouth heat sensitive portion, and lead wires extending respectively from the both ends of the sensor are disposed. The sensor is placed so that the tip ends of the nose heat sensitive portions coincide below the nostrils, and the lead wires are looped over the ears. Then, the sensor is fixed to a position below the nose with a surgical tape or the like, and the tip end of the mouth heat sensitive portion is placed in front of the mouth. According to the configuration, it is possible to measure the temperature of the respiratory gas, and detect the respiratory condition.

(Non-patent Document 1) "Sensor for Analyzing Sleep, Air Flow Sensor (Adult Size) TR-101A", Catalog made on Feb. 23, 2011, Nihon Kohden Corporation, "Search on Mar. 23, 2012", INTERNET <URL:///www.nihonkohden-.co.jp/iryo/documents/pdf/H902599.pdf>

In the temperature sensor, however, the sensor is fixed with a surgical tape, and therefore positionally unstable. Consequently, there is a possibility that positional variation of the sensor may cause the tip ends of the nose heat sensitive portions placed below the nostrils, or the tip end of the mouth heat sensitive portion placed in front of the mouth to be in contact with the skin (living body) or nasal discharge, and hence there arises a case where correct temperature data cannot be stably measured. With respect to oral respiration of a living body, moreover, the manner of opening the mouth, and the like are specific to each living body, and hence it is often that the mouth heat sensitive portion cannot adequately measure the respiratory gas ejected from the mouth. Particularly, it is difficult to measure oral respiration. From the viewpoint that an occurrence of an apnea condition is correctly detected, it is also requested that comprehensive respiration information including not only biological information based on a temperature change of the respiratory gas but also other biological information is to be acquired.

SUMMARY

The presently disclosed subject matter may provide an airway adaptor, biological information acquiring system, and oxygen mask which enable biological information based on a temperature change of a respiratory gas to be correctly acquired, and comprehensive respiration information including other biological information to be surely measured.

The airway adaptor may comprise: a gas passage into which a respiratory gas of a subject is to flow; a respiratory gas introducing portion which is configured to guide the respiratory gas expired from at least one of nostrils and a mouth of the subject, to the gas passage; and an airway case on which a temperature sensor that is configured to detect a temperature change of the respiratory gas flowing into the gas passage is mountable.

The respiratory gas introducing portion may include: a nasal cannula which is configured to guide the respiratory gas expired from the nostrils of the subject, to the gas passage; and a mouth guide which is configured to guide the respiratory gas expired from the mouth of the subject, to the gas passage.

The temperature sensor may include a heat sensitive portion which is configured to sense a temperature, and, when the temperature sensor is mounted on the airway case, the heat sensitive portion may be disposed in at least one of the gas passage and the respiratory gas introducing portion.

The respiratory gas introducing portion may include a branch gas passage which is connectable to a pressure sensor portion for measuring a pressure generated by the respiratory gas.

The respiratory gas introducing portion may be a nasal cannula which is configured to guide the respiratory gas expired from the nostrils of the subject, to the gas passage.

The airway adaptor may further comprise: a carbon dioxide concentration measuring sensor which is configured to detect a concentration of carbon dioxide of the respiratory gas flowing into the gas passage, and which is mountable on the airway case.

The carbon dioxide concentration measuring sensor may include a light measurement supporting portion which is mounted on the airway case. The light measurement supporting portion may include a light-emitting element and a light-receiving element which are mounted on the airway case so as to sandwich the gas passage, and which are opposed to each other on an optical axis across the gas passage. The heat sensitive portion may be disposed at a position which is in the gas passage, and in which the optical axis is not interrupted by the heat sensitive portion.

The temperature sensor may include a temperature measurement supporting portion which is attachable to and detachable from the light measurement supporting portion of the carbon dioxide concentration measuring sensor.

The airway adaptor may further comprise a sample tube which is connected to the respiratory gas introducing portion, which is configured to suck part of the respiratory gas flowing into the gas passage, and which is connectable to a carbon dioxide concentration measuring section that is configured to detect a concentration of carbon dioxide of the sucked respiratory gas.

The respiratory gas introducing portion may include a branch gas passage which is connectable to a pressure sensor portion for measuring a pressure generated by the respiratory gas.

The respiratory gas introducing portion may be a nasal cannula which is configured to guide the respiratory gas expired from the nostrils of the subject, to the gas passage.

The temperature sensor may include a heat sensitive portion which is configured to sense a temperature, and the respiratory gas introducing portion may include a hole in which the heat sensitive portion is enterable.

The respiratory gas introducing portion may be a mouth guide which is configured to guide the respiratory gas expired from the mouth of the subject, to the gas passage.

The biological information acquiring system may comprise: a gas passage into which a respiratory gas of a subject is to flow; a nasal cannula which is configured to guide the respiratory gas expired from nostrils of the subject, to the gas passage; a mouth guide which is configured to guide the respiratory gas expired from a mouth of the subject, to the gas passage; a temperature sensor which is configured to detect a temperature change of the respiratory gas of the subject; an airway case on which the temperature sensor is mountable; and a controller which is configured to control an operation process of the temperature sensor.

The biological information acquiring system may further comprise: a pressure sensor which includes: a branch gas passage which is configured to guide a pressure generated by the respiratory gas expired from the nostrils; a pressure sensor portion; and a respiratory pressure acquiring section. The branch gas passage may be connected to the nasal cannula.

The biological information acquiring system may further comprise: a carbon dioxide concentration measuring sensor which is configured to detect a concentration of carbon dioxide of the respiratory gas of the subject, and which is attachable to the airway case. The controller may control an operation process of the carbon dioxide concentration measuring sensor.

The biological information acquiring system may further comprise: a sample tube which is connected to the nasal cannula, which is configured to suck part of the respiratory gas flowing into the gas passage, and which is connectable to a carbon dioxide concentration measuring section that is configured to detect a concentration of carbon dioxide of the sucked respiratory gas. The controller may control an operation process of the carbon dioxide concentration measuring section.

The temperature sensor may include a heat sensitive portion which is configured to sense a temperature, and the mouth guide may include a hole in which the heat sensitive portion is enterable.

The oxygen mask may comprise: a gas passage into which a respiratory gas of a subject is to flow; a respiratory gas introducing portion which is configured to guide the respiratory gas expired from at least one of nostrils and a mouth of the subject, to the gas passage; an airway case on which a temperature sensor that is configured to detect a temperature change of the respiratory gas flowing into the gas passage is mountable; an oxygen supplying portion; and a patient attachment portion which includes an opening that communicates with external air, and which is to be mounted on an outer circumference of a nose or the nose and mouth of the subject.

The temperature sensor may include a heat sensitive portion which is configured to sense a temperature, and the heat sensitive portion may be disposed in at least one of the gas passage and the respiratory gas introducing portion.

The oxygen mask may further comprise: a respiratory gas exhaust port through which the respiratory gas of the subject is discharged. The temperature sensor may include a heat sensitive portion which is configured to sense a temperature, and the heat sensitive portion may be disposed in the respiratory gas exhaust port.

DETAILED DESCRIPTION OF EXEMPLARY EMBODIMENTS

Hereinafter, embodiments of the airway adaptor, biological information acquiring system, and oxygen mask of the presently disclosed subject matter will be described with reference to the accompanying drawings.

First, a first embodiment of the presently disclosed subject matter will be described with reference to FIGS. 1 to 5.

Figure 1:
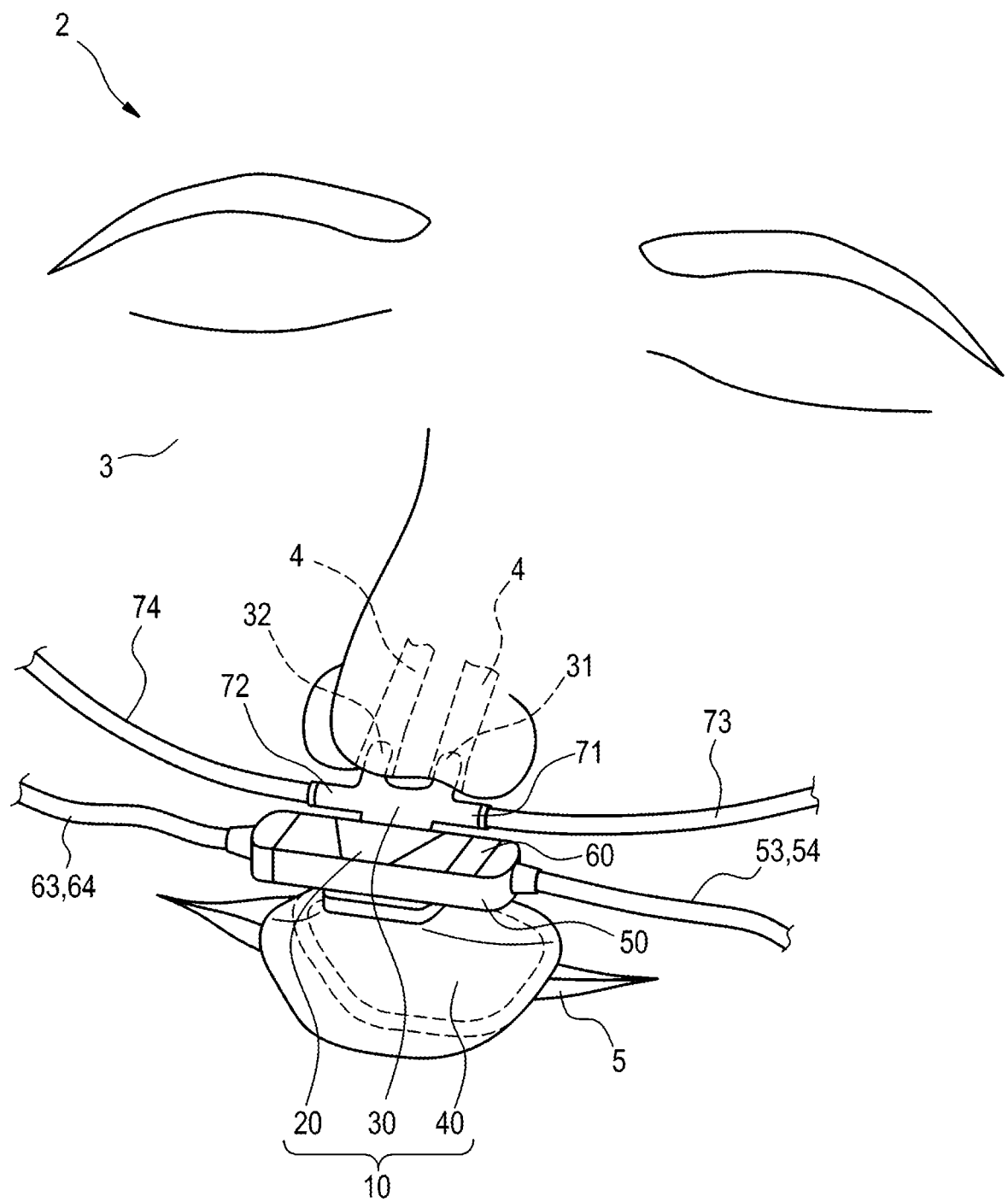
FIG. 1 is a perspective view showing a state where an airway adaptor of a first embodiment of the presently disclosed subject matter is mounted on the face of the subject.

FIG. 1 shows a state where an airway adaptor 10 is mounted on the face 3 of the subject 2. The airway adaptor 10 is an adaptor for acquiring and collecting biological information from respiration of the subject 2.

The airway adaptor 10 includes: an airway case 20 including a gas passage into which the respiratory gas (often referred to as expiration) expired by the subject 2 is to flow; a nasal cannula 30 (an example of the respiratory gas introducing portion) which guides the respiratory gas expired from the nostrils 4 of the subject 2; a mouth guide 40 (an example of the respiratory gas introducing portion) which guides the respiratory gas expired from the mouth 5 of the subject 2; a light measurement supporting portion 50 of a carbon dioxide concentration measuring sensor which is mountable on the airway case 20; a temperature measurement supporting portion 60 of a temperature sensor which is mountable on the light measurement supporting portion 50; and branch gas passages 71, 72 which are formed in the nasal cannula 30.

Figure 2:
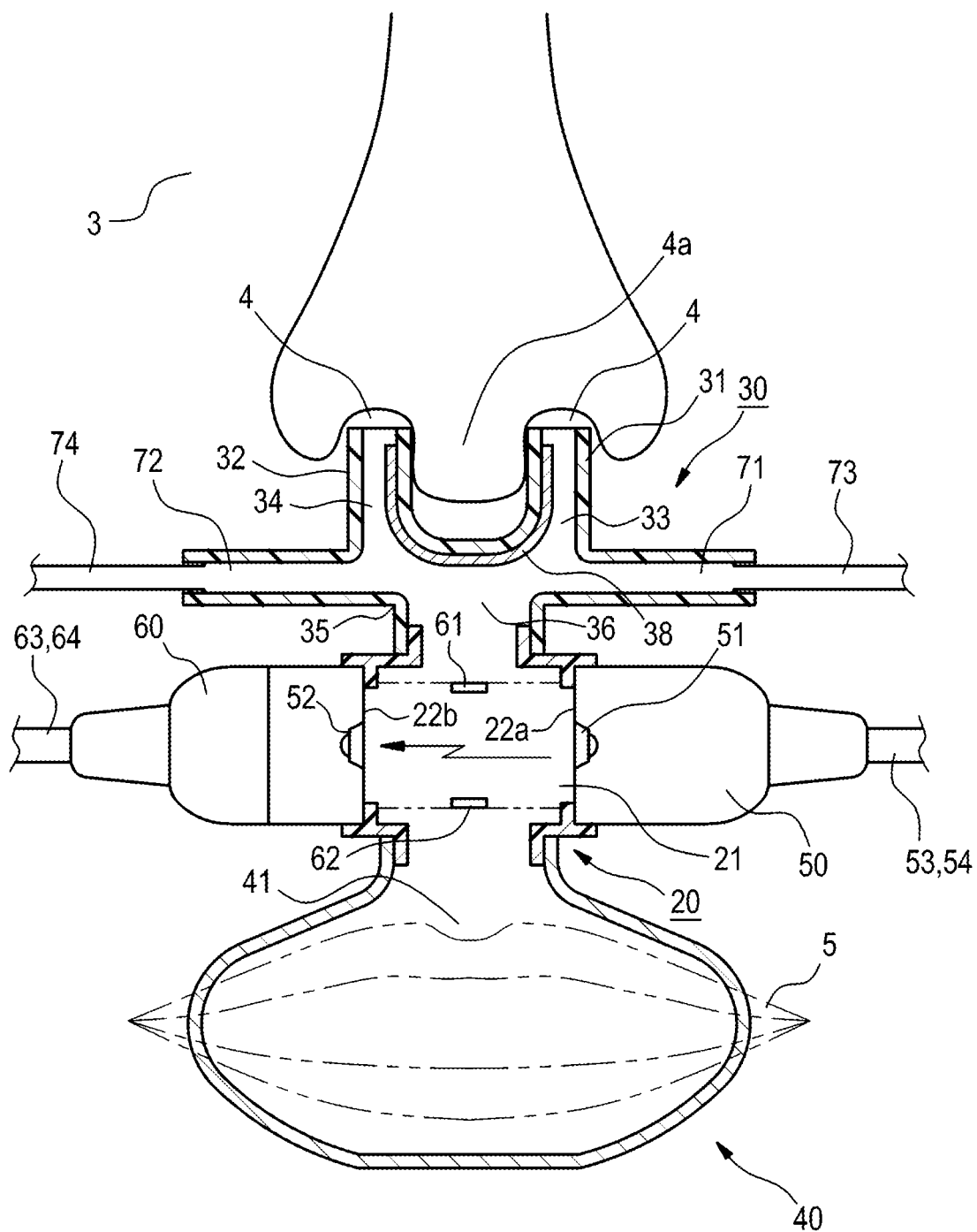
FIG. 2 is a longitudinal sectional view (in the lateral direction of the face) showing the internal structure of the airway adaptor of FIG. 1.

As shown in FIG. 2, the airway case 20 includes a gas passage 21 into which the respiratory gases expired from the nostrils 4 and mouth 5 of the subject 2 are to flow. The airway case 20 further includes supporting portions 23*a*, 23*b* which support the light measurement supporting portion 50 of the carbon dioxide concentration measuring sensor mounted on the airway case 20 (see FIG. 4).

Figure 3:
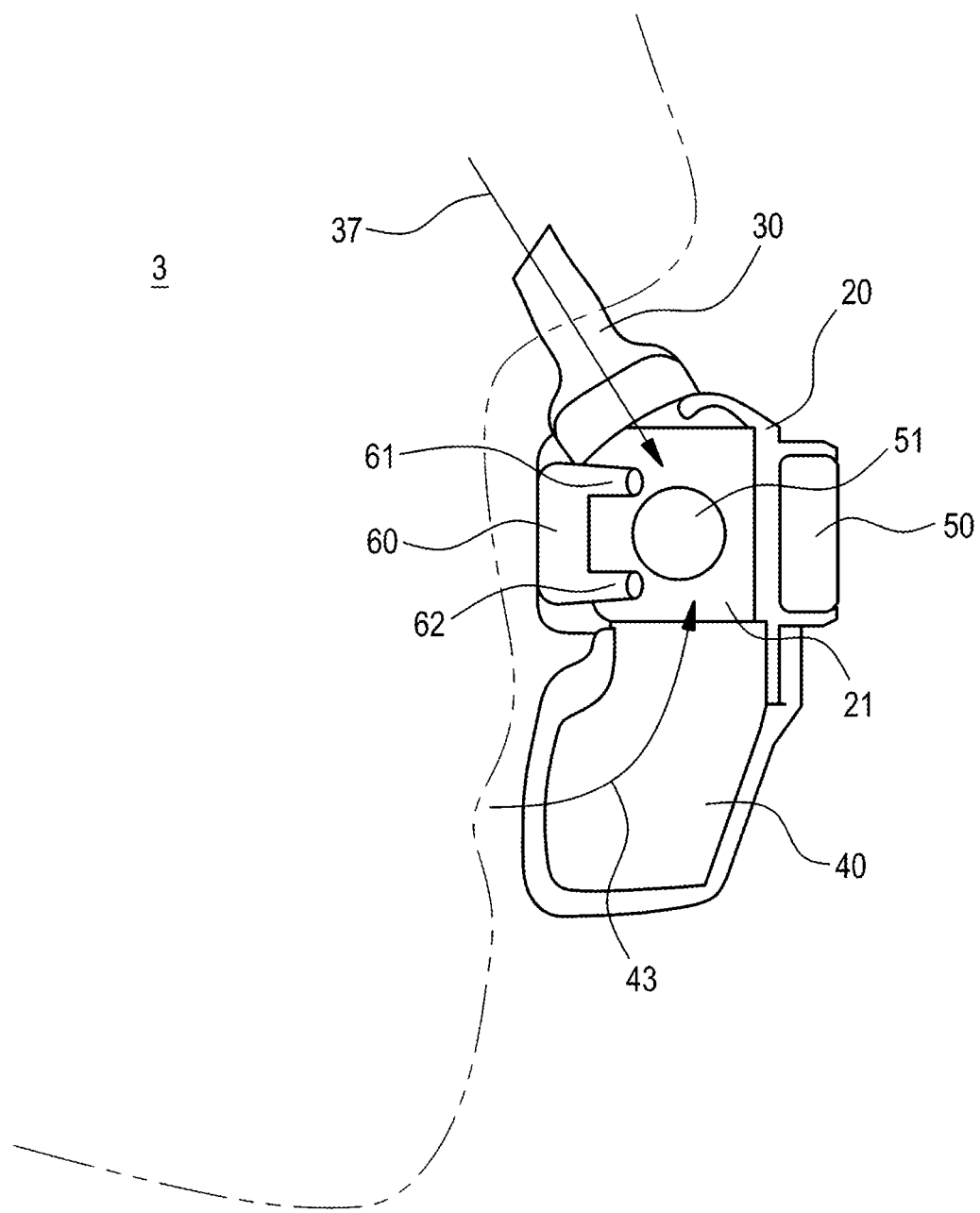
FIG. 3 is a longitudinal sectional view (in the anteroposterior direction of the face) showing the internal structure of the airway adaptor of FIG. 1.

An upper portion of the gas passage 21 is connected to the nasal cannula 30, and its lower portion to the mouth guide 40. According to the configuration, the gas passage 21 functions as a common respiratory gas chamber into which the respiratory gas expired from the nostrils 4, and that expired from the mouth 5 together flow. FIG. 3 diagrammatically shows the flows of the respiratory gases guided into the respiratory gas chamber. The respiratory gas expired from the nostrils 4 flows as indicated by the arrow 37, and that expired from the mouth 5 flows as indicated by the arrow 43.

The nasal cannula 30 has a pair of insertion portions 31, 32 which are used while being inserted into the nostrils 4 of the subject 2. The interiors of the insertion portions 31, 32 are formed as hollow guiding gas passages 33, 34, and a confluent portion 36 is formed in a basal end portion 35 of the passages.

The basal end portion 35 is connected to an upper end portion of the airway case 20, and the confluent portion 36 communicates with the gas passage 21 through an opening which is formed in the upper end portion of the airway case 20. The respiratory gas expired from the nostrils 4 is guided to the gas passage 21 of the airway case 20 while passing through the interiors of the insertion portions 31, 32 and the confluent portion 36.

The insertion portions 31, 32 are configured by a soft material such as silicone rubber, polypropylene, vinyl chloride, or elastomer. The gas passage 21 is a portion which is not to be inserted into the nostrils of the living body, and may include the guiding gas passages 33, 34 and the confluent portion 36.

In the insertion portions 31, 32 of the nasal cannula 30, a support member 38 is disposed along the inner wall extending between the guiding gas passages 33, 34. The support member 38 is formed by a material (for example, a wire) which is plastically deformable. Therefore, the member is deformed by application of a force, and, when the force application is cancelled, maintains the deformed shape. Therefore, the support member 38 causes inner wall parts of the insertion portions 31, 32 which are opposed to the nasal septum 4*a*, to function as plastically deformable parts.

When a force is applied to the insertion portions 31, 32 and the support member 38 is plastically deformed so as to extend along the shape of the surface of the nasal septum 4*a*, the support member 38 maintains the deformed shape even after the force application is cancelled. Therefore, the insertion portions 31, 32 can be prevented from being separated from the nasal septum 4*a*, and the state where the airway adaptor 10 is mounted on the face 3 can be maintained.

The mouth guide 40 is a guiding member for guiding the respiratory gas expired from the mouth 5 of the subject 2 to the gas passage 21 of the airway case 20, and disposed while being connected to a lower portion of the airway case 20. The mouth guide 40 is formed into a dome-like shape as a whole, so that a space is formed in the interior. The space constitutes a guiding gas passage 41.

The guiding gas passage 41 communicates with the gas passage 21 through an opening formed in a lower end portion of the airway case 20. When the airway adaptor 10 is mounted on the face 3 of the subject 2, the mouth guide 40 is placed in front of the mouth 5 of the subject 2. The respiratory gas expired from the mouth 5 is guided to the gas passage 21 of the airway case 20 through the guiding gas passage 41.

Figure 4:
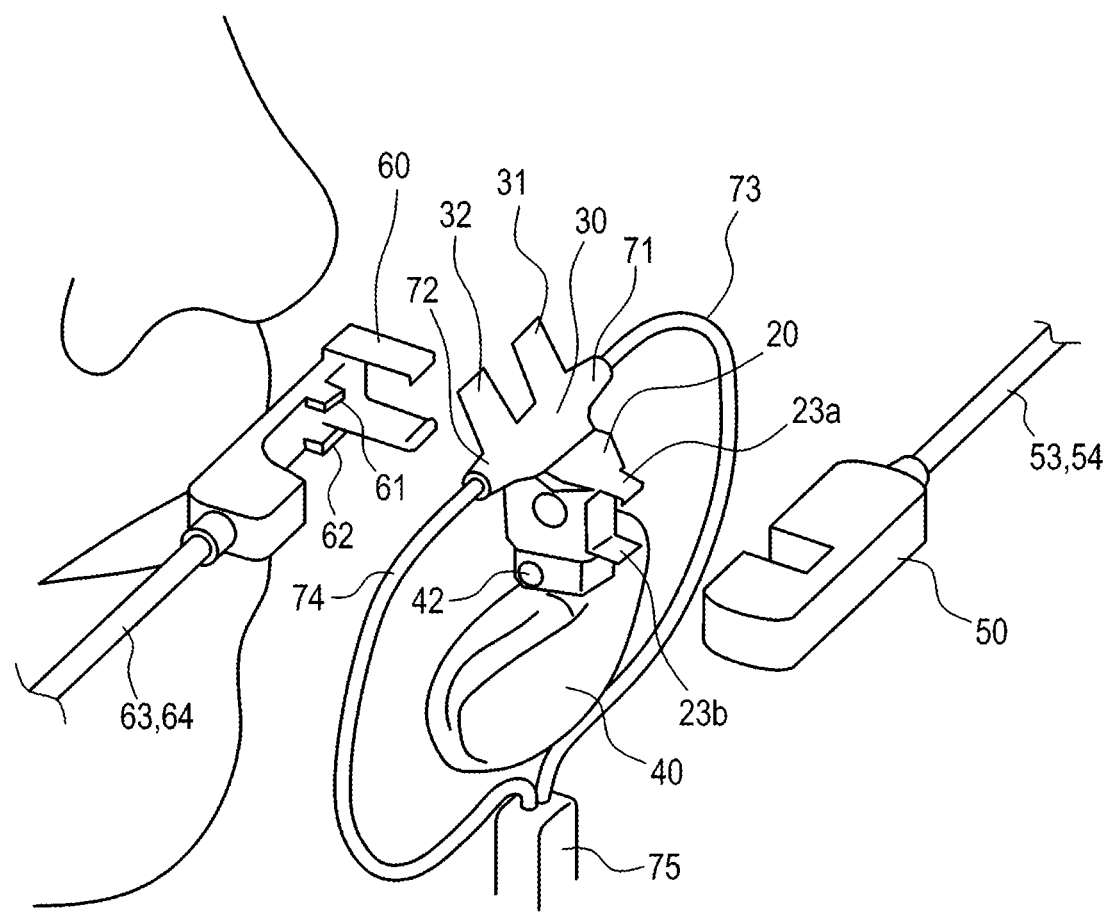
FIG. 4 is an exploded view of the airway adaptor of FIG. 1.

The mouth guide 40 is swingably supported by the airway case 20 through a support shaft 42 (see FIG. 4). When the mouth guide 40 is swung in the anteroposterior direction about the support shaft 42, the position of the mouth guide 40 with respect to the mouth 5 of the subject 2 can be adjusted. The distance between the mouth guide 40 and the mouth 5 can be adequately adjusted so that an appropriate volume of the respiratory gas is guided to the gas passage 21. The gas passage 21 may include the guiding gas passage 41.

The light measurement supporting portion 50 is a member which constitutes a part of the carbon dioxide concentration measuring sensor, and, as shown in FIGS. 3 and 4, mounted on the airway case 20. The light measurement supporting portion 50 is mounted on the airway case 20 so as to be on the both sides of the gas passage 21 of the airway case 20. The mounted light measurement supporting portion 50 is sandwichedly held by the supporting portions 23*a*, 23*b* of the airway case 20. The light measurement supporting portion 50 is disposed so as to be attachable to and detachable from the airway case 20.

As shown in FIG. 2, the light measurement supporting portion 50 includes a light-emitting element 51 and a light-receiving element 52. When the light measurement supporting portion 50 is mounted on the airway case 20, the light-emitting surface of the light-emitting element 51 and the light-receiving surface of the light-receiving element 52 are opposed to the side surfaces of the gas passage 21, respectively. As a result, the light-emitting element 51 and the light-receiving element 52 are opposed to each other on the same optical axis across the gas passage 21.

In this way, the gas passage 21 is formed so as to traverse between the light-emitting element 51 and the light-receiving element 52. In the embodiment, the light-emitting element 51 can be configured by an infrared light source, and the light-emitting element 51 by a photodiode. The light-emitting element 51 and the light-receiving element 52 are connected to a carbon dioxide concentration acquiring section 104 (see FIG. 5) through lead wires 53, 54, respectively.

The temperature measurement supporting portion 60 is a member which constitutes a part of a temperature sensor, and, as shown in FIGS. 3 and 4, mounted on the light measurement supporting portion 50 of the carbon dioxide concentration measuring sensor. The temperature measurement supporting portion 60 is disposed so as to be attachable to and detachable from the light measurement supporting portion 50. The temperature measurement supporting portion 60 includes heat sensitive portions 61, 62 for sensing and detecting a temperature change of the respiratory gas.

The heat sensitive portions 61, 62 are disposed at a number of at least one, in the embodiment, two, in such a manner that, when the temperature measurement supporting portion 60 is mounted on the light measurement supporting portion 50, the heat sensitive portions are disposed in the gas passage 21 of the airway case 20. Although not illustrated, in the case where a plurality of heat sensitive portions are disposed, one (mainly, for the respiratory gas from the nose) may be disposed in the gas passage 21 (which may include the guiding gas passages 33, 34, 41 and the confluent portion 36), and the other (s) (mainly, for the respiratory gas from the mouth) may be disposed in the mouth guide 40.

In the gas passage 21, through holes are formed to pass through the side surface, and, when the temperature measurement supporting portion 60 is mounted, the heat sensitive portions 61, 62 are disposed in the gas passage 21 through the through holes. In the gas passage 21, the heat sensitive portions 61, 62 are disposed in the interior (respiratory gas chamber) of the gas passage into which both the respiratory gas expired from the nostrils, and that expired from the mouth are guided and flown. As shown in FIGS. 2 and 3, furthermore, the heat sensitive portions 61, 62 are disposed at positions where the optical path of light which is expired from the light-emitting element 51 and received by the light-receiving element 52 is not interrupted by the heat sensitive portions 61, 62.

Each of the heat sensitive portions may be configured by, for example, a thermocouple. The heat sensitive portions 61, 62 are connected to a respiratory temperature acquiring section 103 (see FIG. 5) through lead wires 63, 64, respectively. One thermocouple may measure the temperatures of respiratory gases from the nose and the mouth, or two thermocouples may be used for respectively measuring those from the nose and the mouth.

The position to which the temperature measurement supporting portion 60 is mounted is not limited to that shown in the embodiment, and may be a position where conditions for allowing the heat sensitive portions 61, 62 to be disposed in the gas passage 21 (positions where light expired from the light-emitting element toward the light-receiving element is not interrupted) are satisfied.

Therefore, it is not always necessary that the temperature measurement supporting portion 60 is mounted on the light measurement supporting portion 50 of the carbon dioxide concentration measuring sensor. For example, the temperature measurement supporting portion may be mounted on the airway case 20, the nasal cannula 30, or the like. Also in the case where the temperature measurement supporting portion 60 is mounted on the light measurement supporting portion 50, a configuration may be employed where, contrary to the first embodiment, the light measurement supporting portion 50 is mounted on the airway case 20 from the rear (face 3) side of the airway case 20, and the temperature measurement supporting portion 60 is mounted from the front side of the airway case 20. A large number (two or more) of heat sensitive portions may be disposed as far as they satisfy the above-described requirement.

The branch gas passages 71, 72 guide the pressure generated by the respiratory gas expired from the nostrils 4 to a pressure sensor portion 75 (see FIGS. 4 and 5) of a pressure sensor. The branch gas passages 71, 72 communicate in the confluent portion 36 with the guiding gas passages 33, 34 in the insertion portions 31, 32 of the nasal cannula 30, and laterally extend from a basal end portion 35 (root portion) of the insertion portions 31, 32. Namely, the branch gas passages 71, 72 are formed as parts of the nasal cannula 30.

Tubes (made of a vinyl resin) 73, 74 are connected to tip end portions of the branch gas passages 71, 72, respectively, and the tip ends of the tubes 73, 74 are connected to the pressure sensor portion 75. Part of the respiratory gas expired from the nostrils 4 is guided to the branch gas passages 71, 72, and then to the pressure sensor portion 75 through the tubes 73, 74. The branch gas passages 71, 72 may be configured so as to be attachable to and detachable from the nasal cannula 30 (the insertion portions 31, 32).

Figure 5:
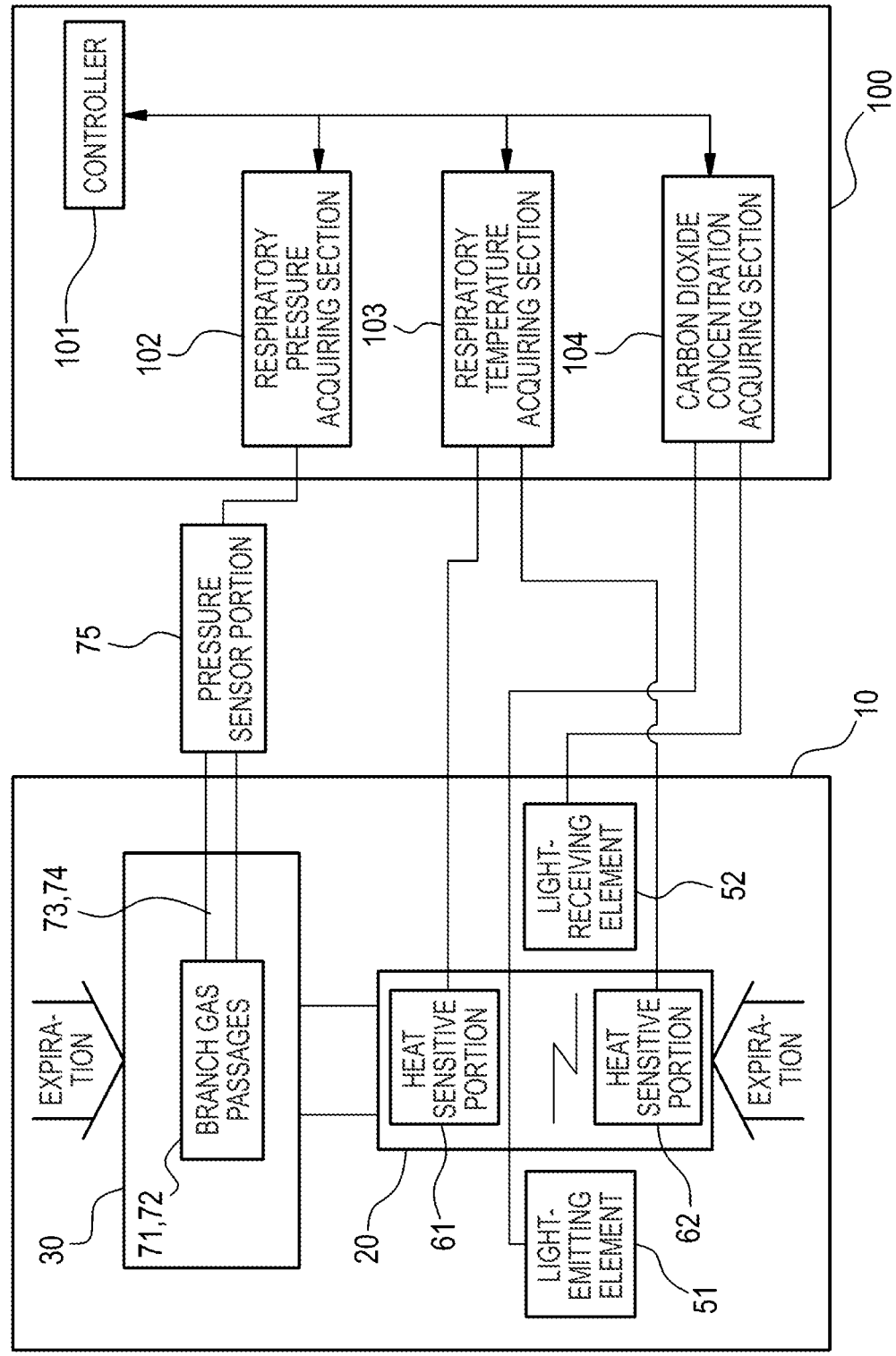
FIG. 5 is a block diagram showing the configuration of a biological information acquiring system of the first embodiment.

FIG. 5 is a block diagram showing the configuration of the biological information acquiring system 1 of the first embodiment.

The heat sensitive portions 61, 62 of the temperature measurement supporting portion 60 which are disposed in the gas passage 21 of the airway case 20 are communicably connected to the respiratory temperature acquiring section 103 disposed in a processing apparatus 100 for processing biological information. The respiratory temperature acquiring section 103 is communicably connected to a controller 101 disposed in the processing apparatus 100.

The controller 101 controls various sections of the biological information acquiring system 1. Although not illustrated, the controller 101 includes: a CPU which governs the control; a ROM which holds programs for executing various process procedures of the CPU; and a memory (a RAM, a flash memory, or the like) which functions as a working area of the CPU, and which stores data acquired by various sections (a respiratory pressure acquiring section 102, the respiratory temperature acquiring section 103, the carbon dioxide concentration acquiring section 104, and the like).

The respiratory temperature acquiring section 103 acquires temperature data in the gas passage 21 which are detected by the heat sensitive portions 61, 62, based on a control signal transmitted from the controller 101. The acquired temperature data are transmitted to the controller 101 to be stored or held in the memory, and displayed on a displaying device (not shown). The respiratory temperature acquiring section 103 monitors signals of temperature data output from the heat sensitive portions 61, 62, so that biological information based on a temperature change of the respiratory gas of the subject 2 can be acquired as respiration information.

Specifically, the respiratory gas expired from the nostrils 4, and that expired from the mouth 5 flow into the gas passage 21. When the respiratory gas expired from at least one of the nostrils 4 and the mouth 5 is guided into the gas passage 21, the temperature in the gas passage 21 is changed. As a result, also the temperatures measured by the heat sensitive portions 61, 62 disposed in the gas passage 21 are changed.

Therefore, for example, a sleep condition (such as an occurrence of an apnea condition) of the subject 2 can be determined by acquiring the temperature data in the gas passage 21 during sleep. The heat sensitive portions 61, 62, the temperature measurement supporting portion 60 including the heat sensitive portions, and the respiratory temperature acquiring section 103 function as the temperature sensor in the presently disclosed subject matter.

The light-emitting element 51 and light-receiving element 52 which are disposed in the light measurement supporting portion 50 are communicably connected to the carbon dioxide concentration acquiring section 104 disposed in the processing apparatus 100. The carbon dioxide concentration acquiring section 104 is further communicably connected to the controller 101 disposed in the processing apparatus 100.

Based on the control signal transmitted from the controller 101, the carbon dioxide concentration acquiring section 104 outputs a light-emitting signal indicative of irradiation of light, to the light-emitting element 51. Upon receiving the light-emitting signal, the light-emitting element 51 emits a light beam (infrared light beam) having a predetermined wavelength. The light beam expired from the light-emitting element 51 propagates across the gas passage 21 to be received by the light-receiving element 52. The light-receiving element 52 outputs an output signal corresponding to the intensity of the received light. The output signal output from the light-receiving element 52 is acquired by the carbon dioxide concentration acquiring section 104.

The acquired output signal (concentration information (concentration data)) is transmitted to the controller 101 to be stored or held in the memory, and displayed on the displaying device (not shown). The carbon dioxide concentration acquiring section 104 monitors the output signal output from the light-receiving element 52, so that biological information based on the concentration of carbon dioxide contained in the respiratory gas of the subject 2 can be acquired as respiration information.

Specifically, when the respiratory gas expired from at least one of the nostrils 4 and mouth 5 of the subject 2 is guided into the gas passage 21 of the airway case 20, the concentration of carbon dioxide in the gas passage 21 is increased. Since the light-emitting surface of the light-emitting element 51, and the light-receiving surface of the light-receiving element 52 are opposed to each other on the same optical axis across the gas passage 21, the infrared light beam expired from the light-emitting element 51 is absorbed by carbon dioxide in the gas passage 21. When the concentration of carbon dioxide in the gas passage 21 is increased, the rate of infrared light at which the infrared light is absorbed by carbon dioxide is raised. Therefore, the intensity of light received by the light-receiving element 52 is lowered, with the result that the state of the output signal output from the light-receiving element 52 is changed.

As described above, the light-emitting element 51, the light-receiving element 52, the light measurement supporting portion 50 including the light-emitting element 51 and the light-receiving element 52, and the carbon dioxide concentration acquiring section 104 function as the carbon dioxide concentration measuring sensor in the presently disclosed subject matter.

The branch gas passages 71, 72 which are laterally extended from the insertion portions 31, 32 of the nasal cannula 30 are connected to the pressure sensor portion 75 through the tubes 73, 74, respectively. The pressure sensor portion 75 is communicably connected to the respiratory pressure acquiring section 102 disposed in the processing apparatus 100. Furthermore, the respiratory pressure acquiring section 102 is communicably connected to the controller 101 disposed in the processing apparatus 100.

Based on the control signal transmitted from the controller 101, the respiratory pressure acquiring section 102 outputs a pressure signal indicative of measurement of the pressure, to the pressure sensor portion 75. Upon receiving the pressure signal, the pressure sensor portion 75 detects the pressure of the respiratory gas supplied from the branch gas passages 71, 72, and supplies a signal indicating the detected pressure, to the respiratory pressure acquiring section 102.

The respiratory pressure acquiring section 102 acquires data of the pressure signal supplied from the pressure sensor portion 75. The acquired pressure data are transmitted to the controller 101 to be stored or held in the memory, and displayed on the displaying device (not shown). The respiratory pressure acquiring section 102 monitors the signal of the pressure data supplied from the pressure sensor portion 75, so that biological information based on the respiratory pressure of the subject 2 can be acquired as respiration information.

Specifically, part of the respiratory gas expired from the nostrils 4 of the subject 2 is guided to the branch gas passages 71, 72, and then passes through the tubes 73, 74 to reach the pressure sensor portion 75. When the respiratory gas expired from the nostrils is guided to the branch gas passages 71, 72, the pressure in the tubes 73, 74 is changed.

The pressure sensor portion 75 detects the pressure variation in the tubes 73, 74, and outputs an electrical signal corresponding to the pressure value. The branch gas passages 71, 72, the tubes 73, 74, the pressure sensor portion 75, and the respiratory pressure acquiring section 102 function as the pressure sensor in the presently disclosed subject matter.

It is not always necessary that the pressure sensor portion 75 is independently disposed outside the processing apparatus 100. The pressure sensor portion may be configured so as to be incorporated in the processing apparatus 100 as a part thereof.

The airway adaptor and biological information acquiring system of the first embodiment of the presently disclosed subject matter are configured as described above, and hence achieve the following effects.

The heat sensitive portions 61, 62 are disposed in the interior (respiratory gas chamber) of the gas passage into which both the respiratory gas expired from the nostrils 4, and that expired from the mouth 5 are guided. Therefore, the respiratory gas expired from the nostrils 4, and that expired from the mouth 5 can be subjected to measurement while using the common heat sensitive portions 61, 62, and biological information based on a temperature change of the respiratory gas can be surely acquired as respiration information.

The heat sensitive portions 61, 62 are disposed in the state where they are housed in the gas passage 21. During a process of acquiring biological information, therefore, respiration information can be stably acquired without causing the heat sensitive portions 61, 62 to be in contact with the living body (the skin of the subject). Particularly, the heat sensitive portions 61, 62 are disposed at the positions which are not inserted into the nostrils. Even when, for example, the subject turns over during sleep, therefore, the possibility that the heat sensitive portions may make contact with the living body is very low. Consequently, respiration information can be stably acquired. Moreover, the influence due to nasal discharge is reduced.

Also when the living body breaths through the mouth, the mouth guide 40 surely guides the respiratory gas to the gas passage, and therefore measurement of a temperature change during oral respiration is accurately realized irrespective of the opened condition of the mouth of the living body.

In the case where one thermocouple is employed to constitute a heat sensitive portion, the production cost can be reduced. In the case where a plurality of thermocouples are employed to constitute heat sensitive portions, when they are used in a mode where a temperature change of the respiratory gas from the nose, and that of the respiratory gas from the mouth are independently measured, nasal respiration and oral respiration can be discriminated from each other.

Since the heat sensitive portions 61, 62 are disposed at positions where the light beam which is expired from the light-emitting element 51 and received by the light-receiving element 52 is not interrupted, biological information based on the concentration of carbon dioxide contained in the respiratory gas can be correctly acquired without causing the heat sensitive portions 61, 62 to obstruct the measurement of the concentration of carbon dioxide by the carbon dioxide concentration measuring sensor.

Since the branch gas passages 71, 72 for the pressure sensor are connected to the insertion portions 31, 32 of the nasal cannula 30, the respiratory gas discharged from the nostrils of the subject 2 is allowed to be guided to the pressure sensor portion 75 through the branch gas passages 71, 72, simply by inserting the insertion portions 31, 32 into the nostrils. Namely, biological information based on the respiratory pressure can be acquired without inserting the branch gas passages 71, 72 into the nostrils. Particularly, not only a temperature change of the respiratory gas, but also the respiratory pressure and the concentration of carbon dioxide of the respiratory gas can be measured simply by inserting the nasal cannula 30 into the nostrils of the living body.

As described above, according to the airway adaptor 10 and the biological information acquiring system 1 of the embodiment, sets of respiration information including biological information of a temperature change, concentration of carbon dioxide, and respiratory pressure of the respiratory gas of the subject can be acquired simultaneously and stably.

Next, a second embodiment of the presently disclosed subject matter will be described with reference to FIG. 6. Components which are identical or similar to those of the airway adaptor 10 and biological information acquiring system 1 of the first embodiment have identical or similar functions and effects, and are denoted by the same reference numerals.

Figure 6:
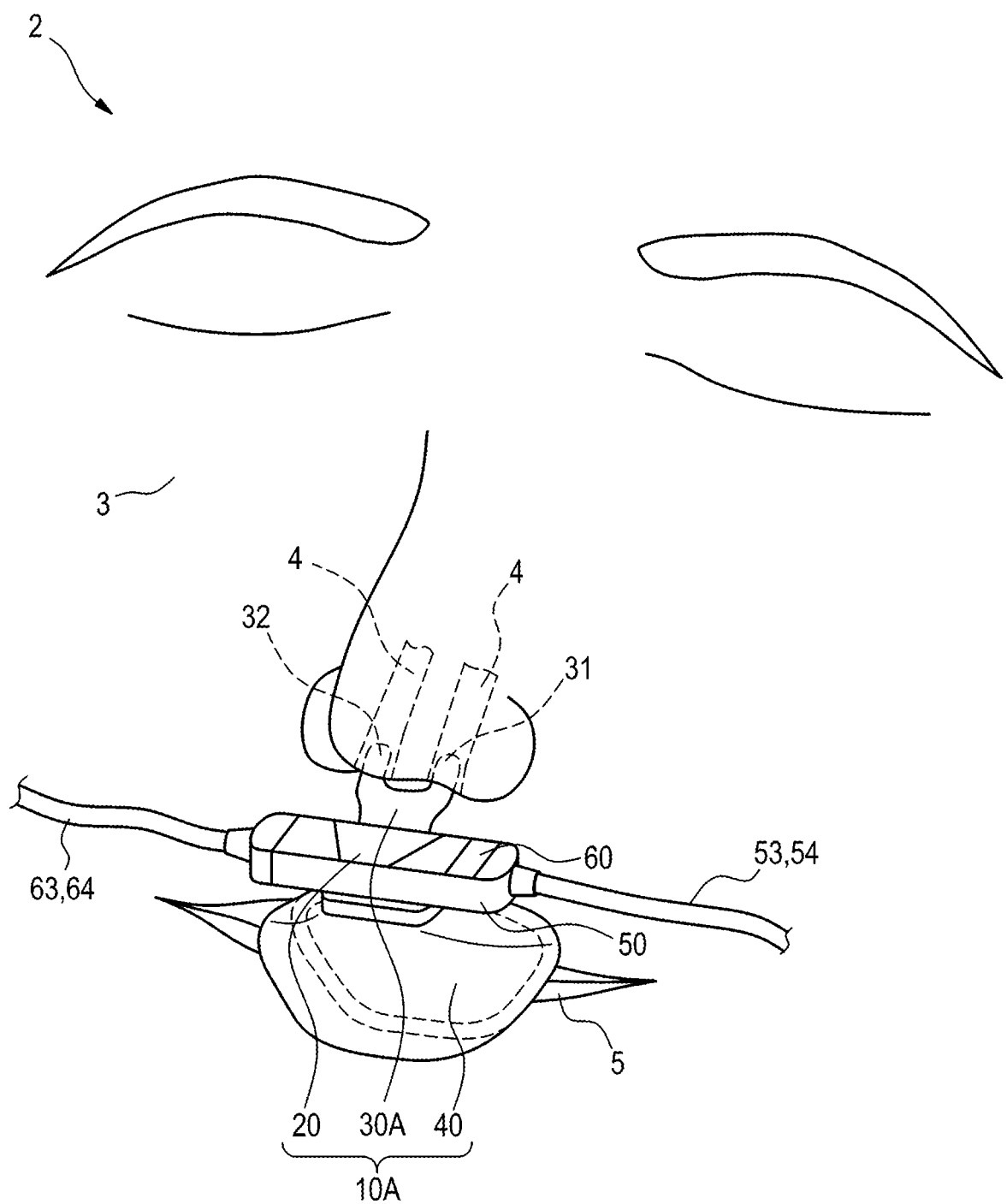
FIG. 6 is a perspective view showing a state where an airway adaptor of a second embodiment of the presently disclosed subject matter is mounted on the face of the subject.

As shown in FIG. 6, an airway adaptor 10A of the second embodiment is different from the airway adaptor 10 of the first embodiment in that the airway adaptor 10A does not include the branch gas passages which guide the respiratory gas expired from the nostrils 4, to the pressure sensor portion. In a nasal cannula 30A in the second embodiment, namely, the insertion portions 31, 32 for guiding the respiratory gas expired from the nostrils 4 the gas passage 21 of the airway case 20 are formed, but branch gas passages for guiding the respiratory gas expired from the nostrils to the pressure sensor portion are not formed. The other configuration is similar to that of the airway adaptor 10 of the first embodiment.

Although not illustrated, the biological information acquiring system of the second embodiment is different from the biological information acquiring system 1 of the first embodiment shown in FIG. 5 in that, in the block diagram of the biological information acquiring system 1, the configuration (the branch gas passages 71, 72, the tubes 73, 74, the pressure sensor portion 75, and the respiratory pressure acquiring section 102) of the pressure sensor which acquires biological information related to the respiratory pressure of the respiratory gas is not provided. Namely, the biological information acquiring system of the second embodiment includes two sensors, i.e., a carbon dioxide concentration measuring sensor and a temperature sensor. The other configuration is similar to that of the biological information acquiring system 1 of the first embodiment.

According to the configuration of the second embodiment, similarly with the first embodiment, biological information based on a temperature change of the respiratory gas can be stably acquired as respiration information, and biological information based on the concentration of carbon dioxide contained in the respiratory gas can be correctly acquired as respiration information.

Next, a third embodiment in which the presently disclosed subject matter is applied to an oxygen mask will be described with reference to FIGS. 7 and 8. The basic configuration in which the heat sensitive portions of the temperature sensor are disposed in the gas passage of the airway case or the respiratory gas introducing portion to which the respiratory gas is guided is similar to that in the above-described first and second embodiments. Components having similar functions are denoted by the same reference numerals, and their description is omitted.

Figure 7:
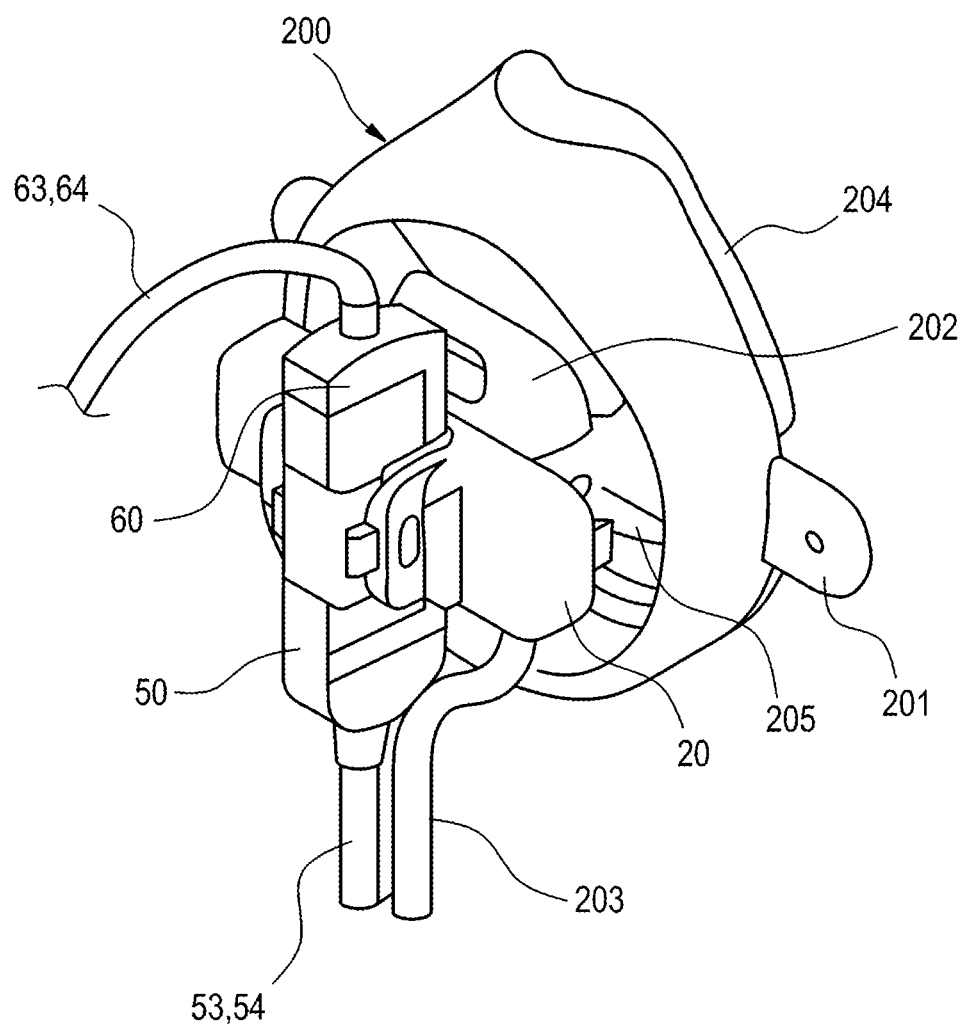
FIG. 7 is a perspective view of an oxygen mask of a third embodiment of the presently disclosed subject matter.

As shown in FIG. 7, an oxygen mask 200 has a mask 201, a respiratory gas introducing portion 202, and an oxygen tube 203 (an example of the oxygen supplying portion). The mask 201 includes an opening which communicates with the external air, and a patient attachment portion 204 which covers the nose and mouth of the patient is disposed in the outer circumferential edge of the opening.

On the surface of the mask 201 which is opposite to the patient attachment portion 204, the airway case 20 is attached to the mask 201. The light measurement supporting portion 50 of the carbon dioxide concentration measuring sensor, and the temperature measurement supporting portion 60 of the temperature sensor which is held on the light measurement supporting portion 50 are attached to the airway case 20.

The oxygen tube 203 is fixed to the airway case 20. In order to prevent the skin of the patient from being dried, preferably, an oxygen blown out port (not shown) is disposed at a position opposed to a scattering plate 205 so that oxygen is not directly blown to the nose and mouth of the patient. The respiratory gas introducing portion 202 guides the respiratory gas expired from the nose or mouth of the patient, to the gas passage 21 of the airway case 20.

Figure 8:
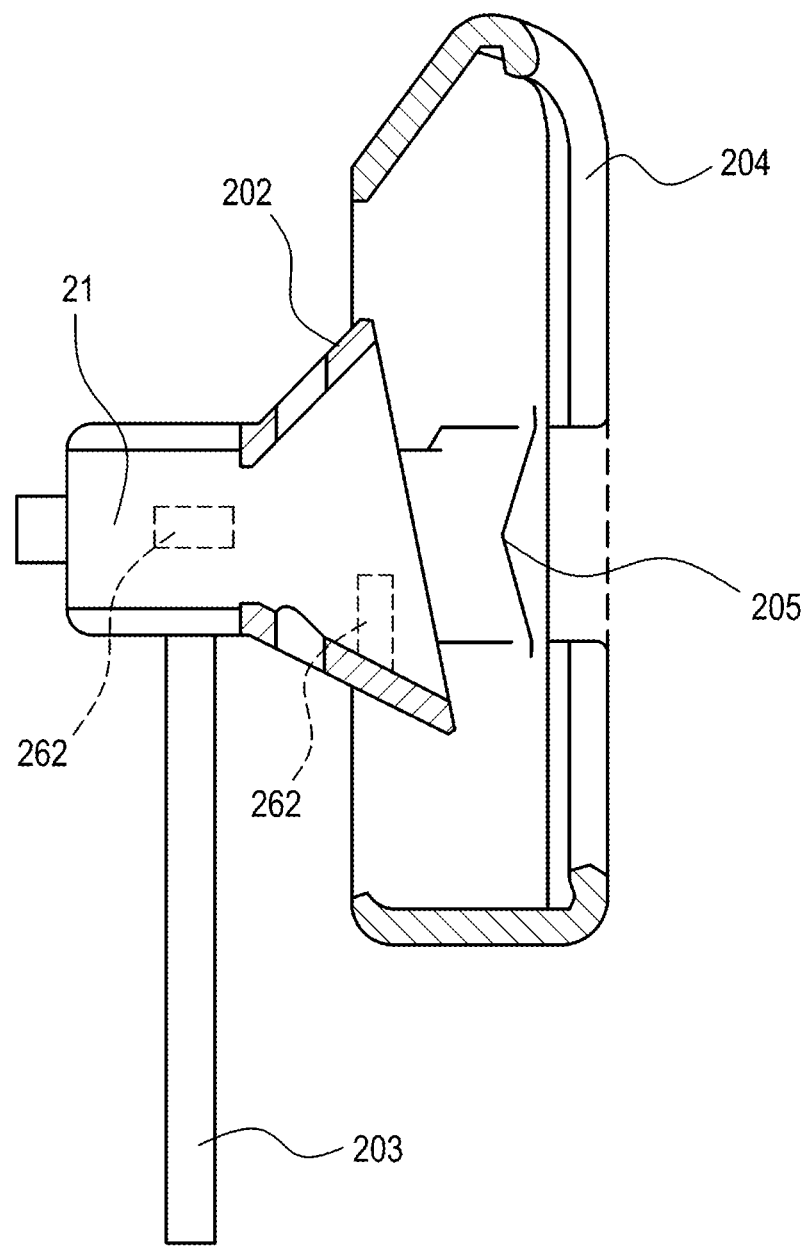
FIG. 8 is a longitudinal sectional view of the oxygen mask.

FIG. 8 is a longitudinal sectional view of the oxygen mask 200 in a state where the carbon dioxide concentration measuring sensor and the temperature sensor are detached. In FIG. 8, the reference numeral 262 indicates an example of regions where, when the temperature sensor is attached to the oxygen mask 200, the heat sensitive portions 61, 62 of the temperature sensor are placed.

In the thus configured oxygen mask 200, similarly with the first and second embodiments, the heat sensitive portions 61, 62 of the temperature sensor are placed in the gas passage 21 or inside the respiratory gas introducing portion 202, and therefore biological information based on a temperature change of the respiratory gas can be stably acquired as respiratory information. Since the oxygen tube 203 for supplying oxygen is placed independently from the gas passage 21 of the airway case 20, moreover, a configuration is attained where the respiratory gas which is the target of the measurement by the heat sensitive portions 61, 62 of the temperature sensor is not affected by the temperature of the oxygen passing through the oxygen tube 203. According to the configuration of the oxygen mask 200, therefore, a temperature change of the respiratory gas of the patient can be accurately measured while supplying oxygen.

Next, an airway adaptor 10B of a fourth embodiment will be described with reference to FIG. 9. Components which are identical or similar to those of the airway adaptor 10 and biological information acquiring system 1 of the first embodiment have identical or similar functions and effects, and are denoted by the same reference numerals.

Figure 9:
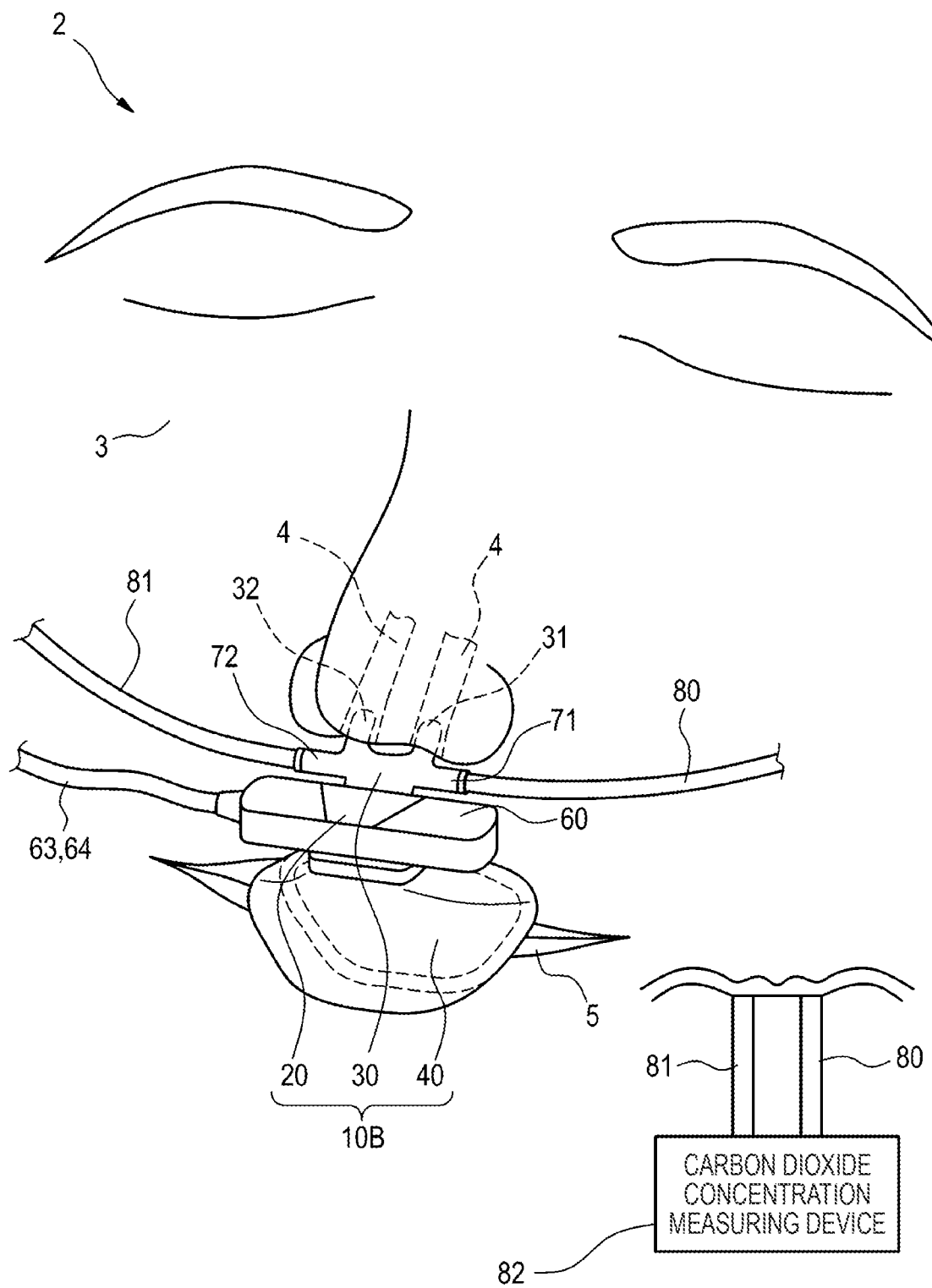
FIG. 9 is a perspective view showing a state where an airway adaptor of a fourth embodiment of the presently disclosed subject matter is mounted on the face of the subject.

As shown in FIG. 9, the airway adaptor 10B of the fourth embodiment is different from the airway adaptor 10 of the first embodiment in that the airway adaptor 10B does not have the light measurement supporting portion 50 of the carbon dioxide concentration measuring sensor, that the temperature measurement supporting portion 60 of the temperature sensor is mounted on the airway case 20, and that the branch gas passages 71, 72 formed in the nasal cannula 30 are not connected to the tubes 73, 74 connected to the pressure sensor portion 75, but connected to sample tubes 80, 81 connected to a carbon dioxide concentration measuring device 82 (an example of the carbon dioxide concentration measuring section) that is disposed separately from the airway adaptor 10B.

In the airway adaptor 10B of the fourth embodiment, namely, the temperature measurement supporting portion 60 is attached to the supporting portions 23a, 23b (see FIG. 4) disposed in the airway case 20, from the front side of the face of the subject, and supported thereby. In the state where the temperature measurement supporting portion 60 is supported by the airway case 20, the heat sensitive portions 61, 62 (see FIG. 4) for sensing and detecting a temperature change of the respiratory gas are disposed in the gas passage 21 of the airway case 20.

As described above, the light measurement supporting portion 50 of the carbon dioxide concentration measuring sensor is not mounted on the airway case 20 of the airway adaptor 10B. In place of the tubes 73, 74 connected to the pressure sensor portion 75, one ends of the sample tubes 80, 81 are connected to the branch gas passages 71, 72 formed in the nasal cannula 30, respectively. The other ends of the sample tubes 80, 81 are connected to the carbon dioxide concentration measuring device 82.

The carbon dioxide concentration measuring device 82 has the same configuration (the configuration including the light-emitting element 51, the light-receiving element 52, the carbon dioxide concentration acquiring section 104, and the controller 101) as the carbon dioxide concentration measuring sensor in the first embodiment, and detects the concentration of carbon dioxide of the respiratory gas. The carbon dioxide concentration measuring device 82 sucks part of the respiratory gas which flows from the nasal cannula 30 into the gas passage of the airway case 20, through the sample tubes 80, 81, and detects the concentration of carbon dioxide of the sucked respiratory gas.

The thus configured airway adaptor 10B has the configuration where, as a sensor, the temperature measurement supporting portion 60 constituting a temperature sensor is simply mounted on the airway case 20, and the components constituting the carbon dioxide concentration measuring sensor are not mounted on the airway case 20. Therefore, the airway adaptor 10B can be simply configured, and reduced in weight.

As a modification of the thus configured airway adaptor 10B, in addition to the branch gas passages 71, 72 to which the sample tubes 80, 81 are connected, other branch gas passages may be formed in the nasal cannula 30, and the tubes 73, 74 connected to the pressure sensor portion 75 may be connected to the other branch gas passages. Also in this configuration, the components constituting the carbon dioxide concentration measuring sensor are not mounted on the airway case 20, and therefore the airway adaptor 10B can be simply configured, and reduced in weight.

Next, an airway adaptor 10C of a fifth embodiment will be described with reference to FIGS. 10 and 11. Components which are identical or similar to those of the airway adaptor 10 and biological information acquiring system 1 of the first embodiment have identical or similar functions and effects, and are denoted by the same reference numerals.

Figure 10:
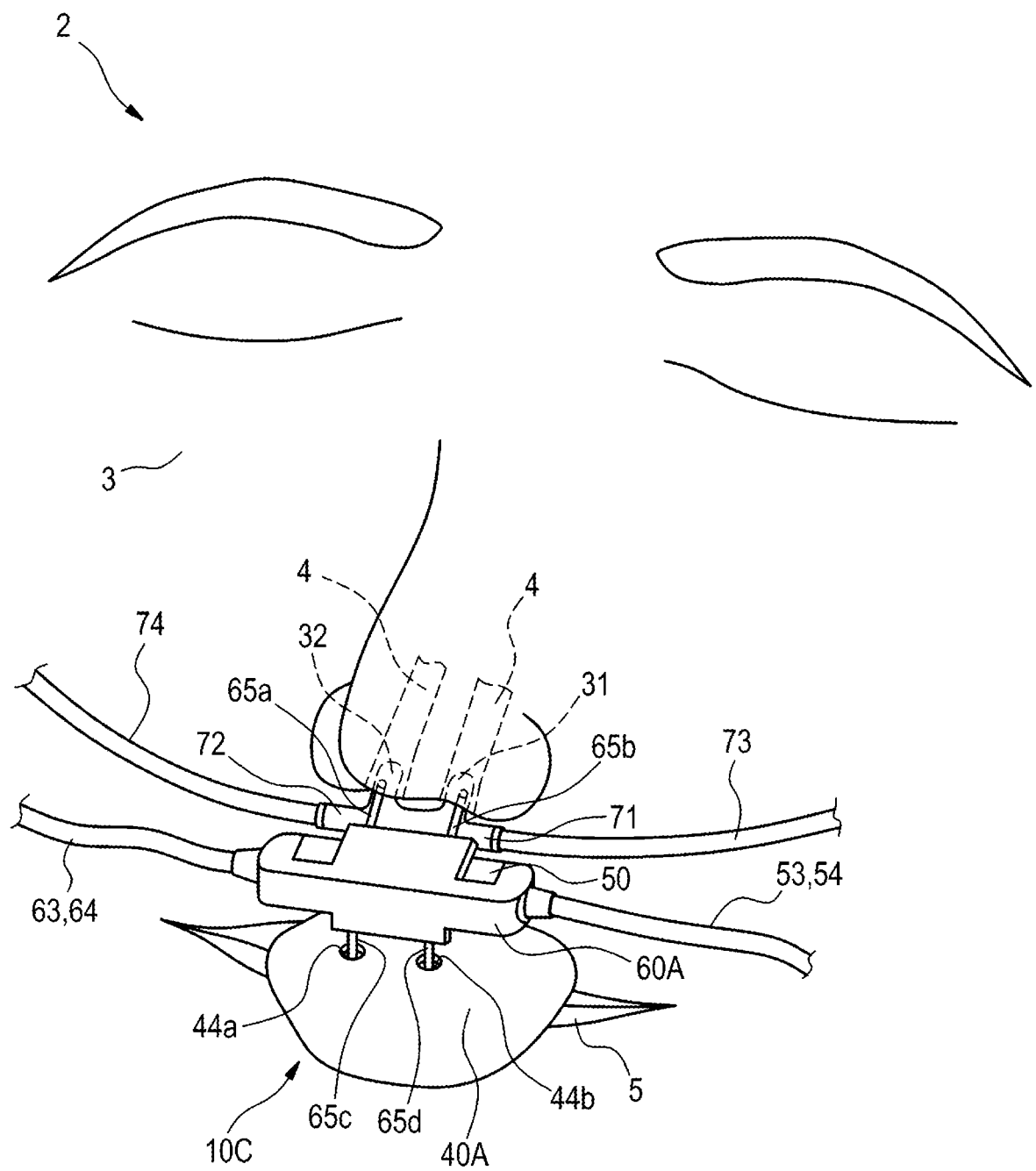
FIG. 10 is a perspective view showing a state where an airway adaptor of a fifth embodiment of the presently disclosed subject matter is mounted on the face of the subject.
Figure 11:
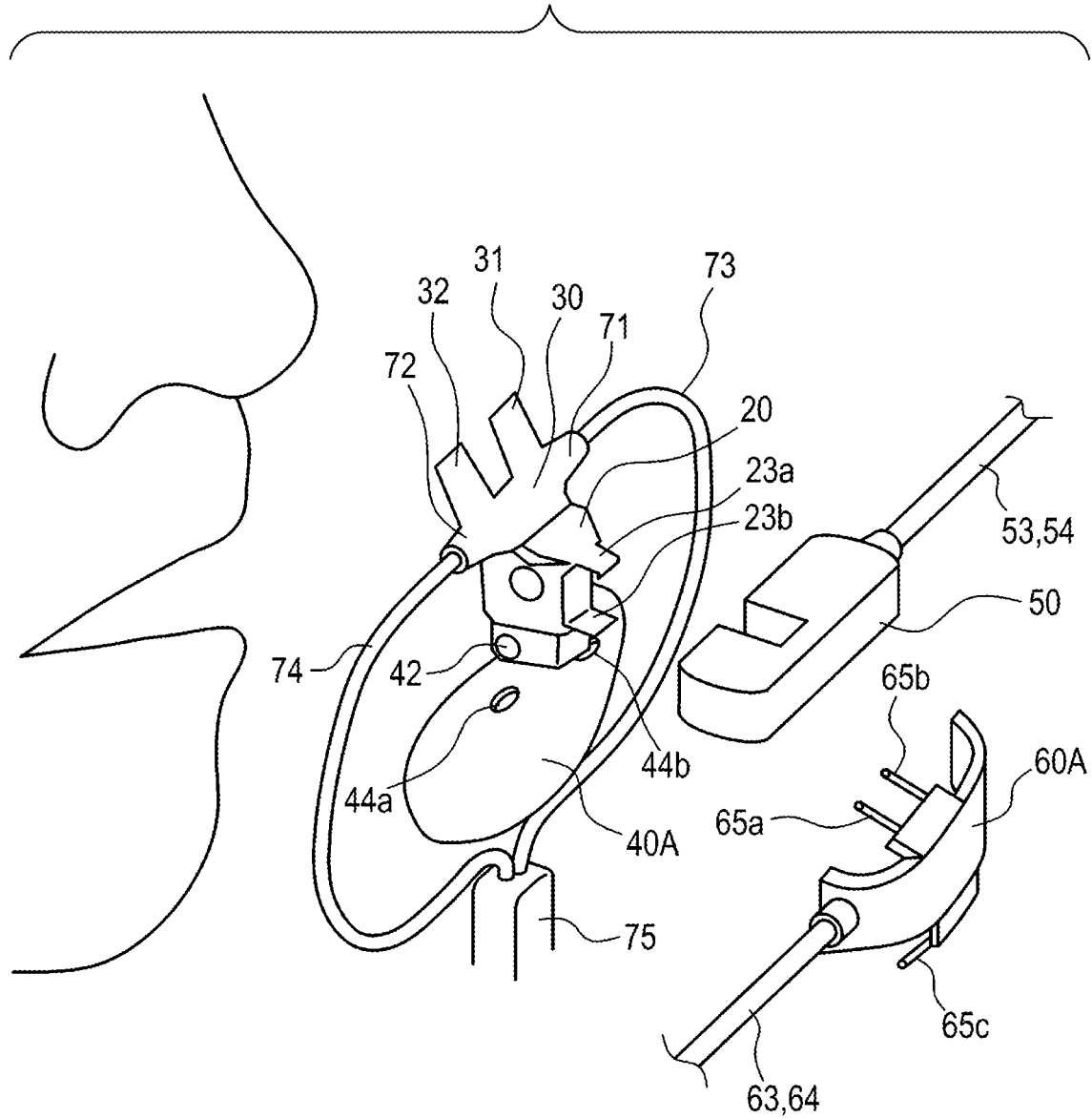
FIG. 11 is an exploded view of the airway adaptor of the fifth embodiment of the presently disclosed subject matter.

As shown in FIGS. 10 and 11, the airway adaptor 10C of the fifth embodiment is different from the airway adaptor 10 of the first embodiment in that holes 44a, 44b are formed in a mouth guide 40A, that a temperature measurement supporting portion 60A is attached to the light measurement supporting portion 50 from the front side of the face of the subject, and that the temperature measurement supporting portion 60A has rod-like heat sensitive portions 65a, 65b which are projected toward the nasal cannula 30, and rod-like heat sensitive portions 65c, 65d which are projected toward the mouth guide 40A.

In the airway adaptor 10C of the fifth embodiment, two through holes 44a, 44b (an example of the hole portion) are formed in the mouth guide 40A.

The temperature measurement supporting portion 60A has the two rod-like heat sensitive portions 65a, 65b which are projected toward the nasal cannula 30 (the upper side of FIG. 10), and the two rod-like heat sensitive portions 65c, 65d which are projected toward the mouth guide 40A (the lower side of FIG. 10). The heat sensitive portions 65a to 65d have the same function as the heat sensitive portions 61, 62 in the first embodiment, and operate as a sensor portion which senses and detects a temperature change of the respiratory gas. The temperature measurement supporting portion 60A is attached to the light measurement supporting portion 50 attached to the airway case 20, from the front side of the face of the subject.

In the state where the temperature measurement supporting portion 60A is mounted on the light measurement supporting portion 50 attached to the airway case 20, the heat sensitive portions 65a, 65b are placed on the insertion portions 31, 32 of the nasal cannula 30. Tip end portions of the heat sensitive portions 65a, 65b are inserted together with the insertion portions 31, 32 into the nostrils 4 of the subject 2, respectively. In this state, the heat sensitive portions 65c, 65d are inserted (plunged) into the holes 44a, 44b formed in the mouth guide 40A, respectively, and tip end portions of the heat sensitive portions 65c, 65d are exposed in the inner space of the mouth guide 40A (the space between the mouth guide and the mouth of the subject).

According to the thus configured airway adaptor 10C, the heat sensitive portions 65a, 65b can measure a temperature change of the respiratory gas expired from the nostrils 4, and the heat sensitive portions 65c, 65d can measure the respiratory gas expired from the mouth 5. Therefore, biological information based on a temperature change of the respiratory gas can be surely acquired as respiration information.

In the configuration where the heat sensitive portions 65a, 65b are placed on the insertion portions 31, 32 of the nasal cannula 30, and the heat sensitive portions 65c, 65d are inserted into the holes 44a, 44b formed in the mouth guide 40A, respiration information can be stably acquired during a process of acquiring biological information without causing the heat sensitive portions 65a to 65d to be in contact with the living body (the skin of the subject).

The temperature measurement supporting portion 60A can be attached to the light measurement supporting portion 50 attached to the airway case 20, from the front side of the face of the subject. Therefore, the work of mounting the airway adaptor 10C on the subject is facilitated.

Although, in the above-described embodiment, the mode where the holes 44a, 44b are formed in the mouth guide 40A has been exemplarily described, the presently disclosed subject matter is not limited to this. For example, another configuration may be employed where holes into which the heat sensitive portions 65a, 65b are to be respectively inserted are formed in the insertion portions 31, 32 of the nasal cannula 30, and the tip end portions of the heat sensitive portions 65a, 65b are exposed through the holes in the hollow portions of the insertion portions 31, 32, respectively.

Next, a sixth embodiment in which the presently disclosed subject matter is applied to an oxygen mask will be described with reference to FIGS. 12A to 12C. The basic configuration of the oxygen mask is similar to that of the third embodiment, and the basic configurations of the airway case, the carbon dioxide concentration measuring sensor, and the temperature sensor are similar to those of the fifth embodiment. Components having similar functions are denoted by the same reference numerals, and their description is omitted.

Figure 12A:
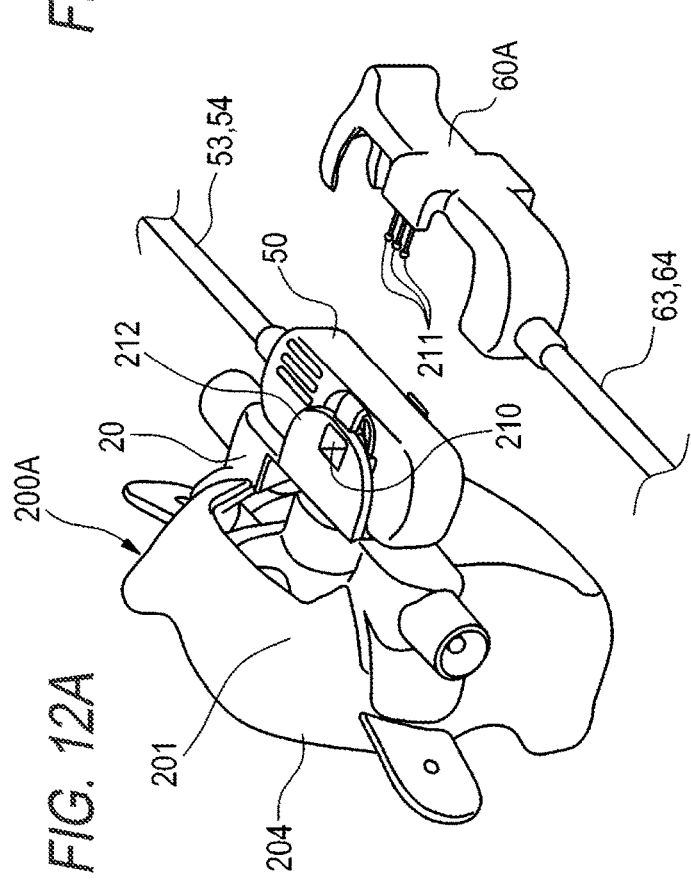
FIG. 12A is an exploded perspective view of an oxygen mask of a sixth embodiment of the presently disclosed subject matter.
Figure 12B:
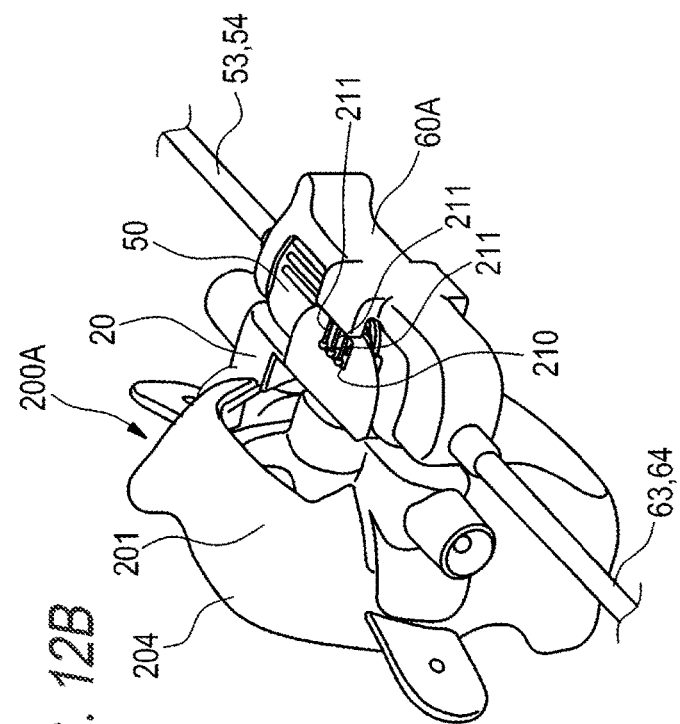
FIG. 12B is a perspective view of the oxygen mask.
Figure 12C:
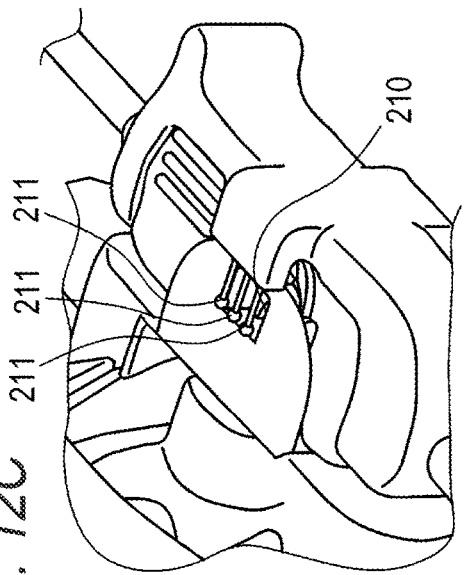
FIG. 12C is a partial enlarged view of the oxygen mask.

As shown in FIGS. 12A to 12C, the airway case 20 is attached to the surface of the mask 201 which is opposite to the patient attachment portion 204. The airway case 20 includes a supporting portion 212 which supports the light measurement supporting portion 50, and an opening 210 (an example of the respiratory gas exhaust port) is formed in a part of the supporting portion 212. The opening 210 communicates with the gas passage 21 of the airway case 20. Part of the respiratory gas discharged from the patient is exhausted from the opening 210.

The temperature measurement supporting portion 60A of the temperature sensor has a plurality of rod-like heat sensitive portions 211. As shown in FIGS. 12B and 12C, in the state where the light measurement supporting portion 50 of the carbon dioxide concentration measuring sensor, and the temperature measurement supporting portion 60A held by the light measurement supporting portion 50 are attached to the airway case 20, the heat sensitive portions 211 are placed above the opening 210. According to the configuration, the heat sensitive portions 211 are exposed to the respiratory gas discharged from the patient, and biological information based on a temperature change of the respiratory gas can be surely acquired as respiration information. According to the configuration, moreover, respiration information can be stably acquired without causing the heat sensitive portions 211 to be in contact with the living body (the skin of the subject).

The presently disclosed subject matter is not limited to the above-exemplified embodiments, and may be adequately changed without departing from the spirit of the presently disclosed subject matter.

According to an aspect of the presently disclosed subject matter, the temperature sensor is incorporated in the airway case, and can measure a temperature change of a respiratory gas introduced into the gas passage, and therefore correct respiration information can be stably measured.

The presently disclosed subject matter is useful in the medical field such as a test for sleep apnea.

What is claimed is:

1. An airway adaptor comprising:
   a gas passage into which a respiratory gas of a subject is to flow;
   a respiratory gas introducing portion which is configured to guide the respiratory gas expired from at least one of nostrils and a mouth of the subject, to the gas passage, and which includes a cup-shaped mouth guide that includes a wall configured to face the mouth of the subject and define an inner cavity so as to retain the respiratory gas from the mouth of the subject therein, and a hole extending through the wall and communicating with the inner cavity;
   an airway case;
   a member mounted to the airway case; and
   a temperature sensor comprising a pair of spaced-apart, arm portions extending away from the temperature sensor, the pair of arm portions configured to hold the member therebetween so that the temperature sensor is mounted on the airway case via the member, the temperature sensor including a base portion that is disposed outside of the inner cavity and a heat sensitive portion that extends into the inner cavity through the hole so that a tip end portion of the heat sensitive portion is exposed in the inner cavity for detecting a temperature change of the respiratory gas expired from at least one of the nostrils and the mouth of the subject or provided in the gas passage for detecting a temperature change of the respiratory gas flowing into the gas passage.

2. The airway adaptor according to claim 1, wherein the respiratory gas introducing portion includes:
   a nasal cannula which is configured to guide the respiratory gas expired from the nostrils of the subject, to the gas passage; and
   the mouth guide which is configured to guide the respiratory gas expired from the mouth of the subject, to the gas passage.

3. The airway adaptor according to claim 1, wherein the respiratory gas introducing portion includes a branch gas passage which is connectable to a pressure sensor portion for measuring a pressure generated by the respiratory gas.

4. The airway adaptor according to claim 3, wherein the respiratory gas introducing portion is a nasal cannula which is configured to guide the respiratory gas expired from the nostrils of the subject, to the gas passage.

5. The airway adaptor according to claim 1, further comprising:
   a carbon dioxide concentration measuring sensor which is configured to detect a concentration of carbon dioxide of the respiratory gas flowing into the gas passage, and which is mountable on the airway case.

6. The airway adaptor according to claim 5, wherein when the heat sensitive portion extends into the gas passage,
   the carbon dioxide concentration measuring sensor includes a light measurement supporting portion which is the member,
   the light measurement supporting portion includes a light-emitting element and a light-receiving element which are mounted on the airway case so as to sandwich the gas passage, and which are opposed to each other on an optical axis across the gas passage, and
   the heat sensitive portion is disposed at a position which is in the gas passage, and in which the optical axis is not interrupted by the heat sensitive portion.

7. The airway adaptor according to claim 6, wherein the temperature sensor includes a temperature measurement supporting portion which is attachable to and detachable from the light measurement supporting portion of the carbon dioxide concentration measuring sensor and which includes the pair of arm portions.

8. The airway adaptor according to claim 1, further comprising:
   a sample tube which is connected to the respiratory gas introducing portion, which is configured to suck part of the respiratory gas flowing into the gas passage, and which is connectable to a carbon dioxide concentration measuring section that is configured to detect a concentration of carbon dioxide of the sucked respiratory gas.

9. The airway adaptor according to claim 8, wherein the respiratory gas introducing portion includes a branch gas passage which is connectable to a pressure sensor portion for measuring a pressure generated by the respiratory gas.

10. The airway adaptor according to claim 9, wherein the respiratory gas introducing portion is a nasal cannula which is configured to guide the respiratory gas expired from the nostrils of the subject, to the gas passage.

11. The airway adaptor according to claim 1, wherein the mouth guide is configured to guide the respiratory gas expired from the mouth of the subject, to the gas passage.

12. The airway adaptor according to claim 1, wherein a second heat sensitive portion is configured to project into the gas passage through a through hole formed in a side face of the gas passage.

13. The airway adaptor according to claim 1, wherein the heat sensitive portion is a rod-like shaped portion of the temperature sensor.

14. The airway adaptor according to claim 1, wherein a diameter of the hole is larger than a diameter of the heat sensitive portion.

15. A biological information acquiring system comprising:
a gas passage into which a respiratory gas of a subject is to flow;
a nasal cannula which is configured to guide the respiratory gas expired from nostrils of the subject, to the gas passage;
a mouth guide which is configured to guide the respiratory gas expired from a mouth of the subject, to the gas passage, the mouth guide including a cup-shaped portion having a wall configured to face the mouth of the subject and define an inner cavity so as to retain the respiratory gas from the mouth of the subject therein and a hole extending through the wall and communicating with the inner cavity;
a temperature sensor including a base portion that is disposed outside of the inner cavity and a heat sensitive portion that extends into the inner cavity through the hole so that a tip end portion of the heat sensitive portion is exposed in the inner cavity for detecting a temperature change of the respiratory gas expired from the mouth or provided in the gas passage for detecting a temperature change of the respiratory gas flowing into the gas passage;
an airway case;
a member mounted to the airway case, wherein a pair of spaced-apart, arm portions extending away from the temperature sensor are configured to hold the member therebetween so that the temperature sensor is mounted on the airway case via the member; and
a controller which is configured to control an operation process of the temperature sensor.

16. The biological information acquiring system according to claim 15, further comprising:
a pressure sensor which includes: a branch gas passage which is configured to guide a pressure generated by the respiratory gas expired from the nostrils; a pressure sensor portion; and a respiratory pressure acquiring section, wherein
the branch gas passage is connected to the nasal cannula.

17. The biological information acquiring system according to claim 15, further comprising:
a carbon dioxide concentration measuring sensor which is configured to detect a concentration of carbon dioxide of the respiratory gas of the subject, and which is attachable to the airway case, wherein
the controller controls an operation process of the carbon dioxide concentration measuring sensor.

18. The biological information acquiring system according to claim 15, further comprising:
a sample tube which is connected to the nasal cannula, which is configured to suck part of the respiratory gas flowing into the gas passage, and which is connectable to a carbon dioxide concentration measuring section that is configured to detect a concentration of carbon dioxide of the sucked respiratory gas, wherein
the controller controls an operation process of the carbon dioxide concentration measuring section.

19. The biological information acquiring system according to claim 15, wherein a second heat sensitive portion is configured to project into the gas passage through a through hole formed in a side face of the gas passage.

20. The biological information acquiring system according to claim 15, wherein the heat sensitive portion is a rod-like shaped portion of the temperature sensor.

21. The biological information acquiring system according to claim 15, wherein a diameter of the hole is larger than a diameter of the heat sensitive portion.

22. An oxygen mask comprising:
a gas passage into which a respiratory gas of a subject is to flow;
a respiratory gas introducing portion which is configured to guide the respiratory gas expired from at least one of nostrils and a mouth of the subject, to the gas passage, and which includes a cup-shaped mouth guide that includes a wall configured to face the mouth of the subject and define an inner cavity so as to retain the respiratory gas from the mouth of the subject therein, and a hole extending through the wall and communicating with the inner cavity;
an airway case;
a member mounted to the airway case;
a temperature sensor comprising a pair of spaced-apart, arm portions extending away from the temperature sensor, the pair of arm portions configured to hold the member therebetween so that the temperature sensor is mounted on the airway case via the member, the temperature sensor including a base portion that is disposed outside of the inner cavity and a heat sensitive portion that extends into the inner cavity through the hole so that a tip end portion of the heat sensitive portion is exposed in the inner cavity for detecting a temperature change of the respiratory gas expired from at least one of the nostrils and the mouth of the subject or provided in the gas passage for detecting a temperature change of the respiratory gas flowing into the gas passage;
an oxygen supplying portion; and
a patient attachment portion which includes an opening that communicates with external air, and which is to be mounted on an outer circumference of a nose or the nose and mouth of the subject.

23. The oxygen mask according to claim 22, wherein a second heat sensitive portion is configured to project into the gas passage through a through hole formed in a side face of the gas passage.

24. The oxygen mask according to claim 22, wherein the heat sensitive portion is a rod-like shaped portion of the temperature sensor.

25. The oxygen mask according to claim 22, wherein a diameter of the hole is larger than a diameter of the heat sensitive portion.

26. An airway adaptor comprising:
a gas passage into which a respiratory gas of a subject is to flow;
a respiratory gas introducing portion which is configured to guide the respiratory gas expired from at least one of nostrils and a mouth of the subject, to the gas passage, and which includes a cup-shaped mouth guide that includes a wall configured to face the mouth of the subject and define an inner cavity so as to retain the respiratory gas from the mouth of the subject therein, and a hole extending through the wall and communicating with the inner cavity;
an airway case;
a light measurement supporting portion mounted to the airway case; and
a temperature sensor comprising a pair of spaced-apart, arm portions extending away from the temperature sensor, the pair of arm portions configured to hold the light measurement supporting portion therebetween so that the temperature sensor is mounted on the airway case via the light measurement supporting portion, the temperature sensor including a base portion that is disposed outside of the inner cavity and a heat sensitive portion that extends into the inner cavity through the hole so that a tip end portion of the heat sensitive portion is exposed in the inner cavity for detecting a temperature change of the respiratory gas expired from at least one of the nostrils and the mouth of the subject or provided in the gas passage for detecting a temperature change of the respiratory gas flowing into the gas passage.

* * * * *